United States Patent [19]

Van den Berg et al.

[11] Plant 4,691

[45] Apr. 14, 1981

[54] IMPATIENS PLANT

[75] Inventors: Cornelis P. Van den Berg; James C. Mikkelsen, both of Ashtabula, Ohio

[73] Assignee: Mikkelsens, Inc., Ashtabula, Ohio

[21] Appl. No.: 103,089

[22] Filed: Dec. 12, 1979

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

An impatiens plant known by the cultivar name Astro, and particularly characterized as to novelty by the combined characteristics of good self-branching; shiny dark metallic green-red foliage with slight variegation; large bicolored light pink and red flowers contrasting with the foliage; floriferous; and excellent keeping quality if grown outdoors in full sunlight.

1 Drawing Figure

The present invention relates to a new and distinct cultivar of impatiens plant, hereinafter referred to by the cultivar name Astro.

Astro is the product of a planned breeding program and was originated from a cross made by us in Ashtabula, Ohio. The seed parent was Star War, an unpatented cultivar, and the pollen parent was Galaxy, likewise unpatented. Asexual reproduction by terminal or stem cuttings taken by us in Ashtabula, Ohio has shown that the combination of unique characteristics as herein disclosed for Astro are stable and retained through successive generations of asexual reproduction.

The following characteristics distinguish Astro from both its parent varieties and other cultivated impatiens of this type known and used in the floriculture industry:

1. Astro was selected especially for the combination of flower color and foliage color, and its outstanding keeping quality outside in full sunlight.
2. Flower color is bicolored light pink with red, similar to that of Star War.
3. Flowers appear in a rather early stage of plant development, and plant continues to flower abundantly throughout the growing season.
4. Flowers are larger than those of Star War.
5. Astro flowers earlier than Galaxy and somewhat later than Star War.
6. Foliage is shiny dark, metallic green-red; older plants exhibit a slight variegation.
7. Foliage size is medium, slightly larger than that of Star War and smaller than that of Galaxy.
8. Astro is faster growing than Star War and comparable in growth rate to Galaxy.
9. Upright growth habit is similar to that of Star War.
10. Cultivar exhibits excellent keeping qualities if grown outside in full sunlight, as tested in Ashtabula, Ohio, where it will flower from planting date in early June until frost kills the plant.

The accompanying colored photograph illustrates the flower and foliage colors of Astro, with the colors being as true as it is reasonably possible to obtain in a colored reproduction of this type.

The following is a detailed description of Astro based on plants produced under commercial practices in Ashtabula, Ohio both in the greenhouses of Mikkelsens Inc. and outdoors in full sunlight. Color references are made to the Royal Horticultural Society Colour Chart except where general terms of ordinary dictionary significance are used.

Parentage: A controlled cross of the cultivar Star War as the seed parent and the cultivar Galaxy as the pollen parent.

Propagation:

(A) *Type cutting.*—Short tip cutting with stems up to 2 cm. long.

(B) *Time to root.*—10–12 days at 20° C. summer. 14–16 days at 20° C. winter.

(C) *Rooting habit.*—Abundant, fibrous.

Plant description:

(A) *Form.*—Upright, self-branching herb, producing a plant approximately 40 cm. high and 60 cm. in diameter when grown outside, starting from a 10 cm. pot, in approximately 60 days.

(B) *Habit of growth.*—Rate of growth moderate to fast for this type of plant. Vegetative shoots are formed at the lower nodes, flowers at the higher nodes.

(C) *Foliage description.*—Lower leaves opposite; higher leaves in whorls of 3 to 7, sometimes more; leaves are simple. (1) Size: Average full grown leaf 120 mm. long×33 mm. wide. Full grown leaves have petioles up to 20 mm. long, young leaves very short to no petioles. (2) Shape: Elliptic, apex acuminate, base attenuate. (3) Texture: Leathery, glabrous. (4) Margin: Ciliate to very slightly serrulate. (5) Color: Young foliage; top side brown 200 B. Under side greyed purple 187-A. Mature foliage; top side yellow green 147A. Under side greyed purple 187A-B. Mature foliage has wedge-shaped area along the mid vein of yellow, infused with green and red. (6) Venation: Pinnate. Main vein greyed-purple 185A.

Flowering description:

(A) *Flowering habits.*—Very floriferous under high light conditions, with single flowers occurring progressively around the whorl of leaves.

(B) *Natural flowering season.*—Flowering is indeterminate and occurs throughout the year.

(C) *Flower buds.*—Conical, covered with 3 sepals. Upper 2 sepals 10 mm. long×5 mm. wide, strongly acuminate; lower sepal 12 mm. long×14 mm. wide, petaloid, asymmetrically funnelform, cuspidate, with a hollow, nearly colorless spur, 45 mm. long if full grown.

(D) *Flowers borne.*—On pedicels, color yellow-green 154D, 60 mm. long.

(E) *Quantity of flowers.*—One flower per leaf, occurring progressively around the whorl of leaves.

(F) *Petals.*—(1) Shape: Top petal heart-shaped with wide base; lower petals heart-shaped. (2) Color: Top side in winter when opening white infused with red-purple to red-purple 62D. Higher concentration of red-purple in the center of the top petal. Two lower petals have a red-purple 58B area at the base, forming an "eye", fading to nearly white; under side red-purple 62D with a lengthwise stripe red-purple 58B in the middle of the petals. Higher concentration of red-purple near the center. (3) Number of petals: Five. (4) Size of petals: Top petal 22 mm. long×30 mm. wide; 2 middle petals 25 mm. long×20 mm. wide; 2 lower petals 30 mm. long×26 mm. wide. Flower size 55 mm. in total diameter.

(G) *Reproductive organs.*—(1) Stamens: Number, five. (a) Anthers: Hooded; top anthers have red-purple spots, others near colorless; (b) Pollen color: Cream; (c) Stamens united in an asymmetrical tube, covering the ovary. Lower stamen shorter than the others. (2) Pistels (a) Stigma: 5 pointed star, colorless, infused with red; (b) Style shape: Very short, dome-shaped; (c) Style color: Colorless, infused with red; (d) Ovary: Size 5 mm. long; color, base green, apex dark red, five celled, explosively dehiscent.

Disease resistance: No general plant diseases observed to date. However, two dotted spider mite can cause plant injury, and thrips can cause injury and stunting of the growing tip.

We claim:

1. A new and distinct cultivar of Impatiens known by the cultivar name Astro, as illustrated and described, and particularly characterized as to novelty by the combined characteristics of good self-branching; shiny dark metallic green-red foliage with slight variegation; large bicolored light pink and red flowers contrasting with the foliage; floriferous; and excellent keeping quality if grown outdoors in full sunlight.

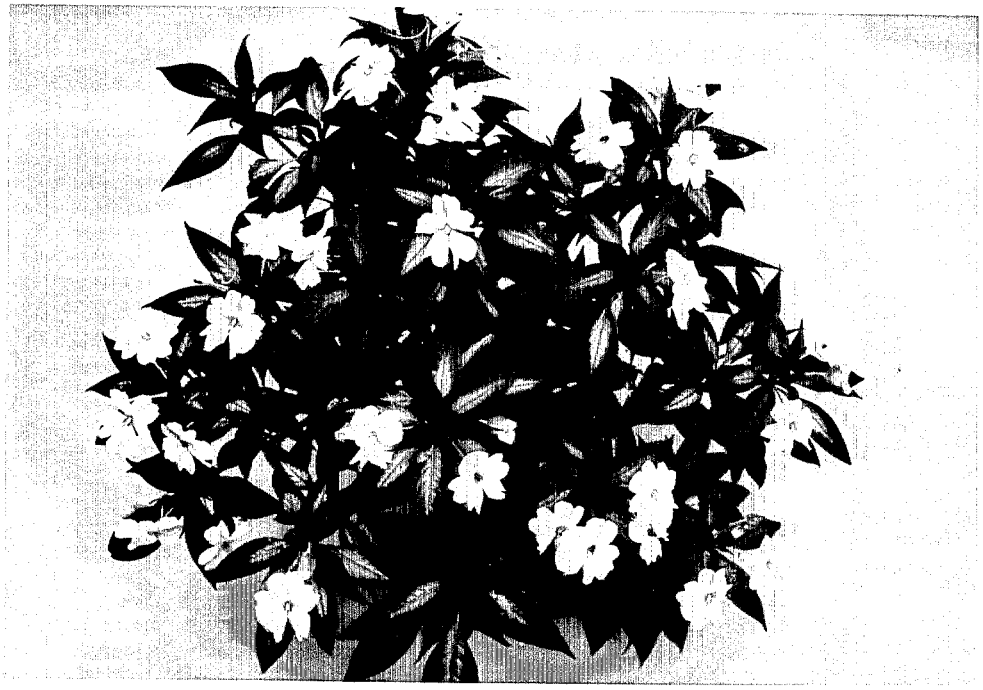

* * * * *